United States Patent
Bornzin et al.

(10) Patent No.: US 7,725,181 B1
(45) Date of Patent: May 25, 2010

(54) APNEA BURDEN MINIMIZING CARDIAC STIMULATION DEVICE

(75) Inventors: Gene A. Bornzin, Simi Valley, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 435 days.

(21) Appl. No.: 11/291,310

(22) Filed: Nov. 30, 2005

(51) Int. Cl.
*A61N 1/00* (2006.01)

(52) U.S. Cl. .......................................... 607/9

(58) Field of Classification Search ............ 607/2, 607/9, 17, 42
See application file for complete search history.

(56) References Cited

U.S. PATENT DOCUMENTS

| | | | |
|---|---|---|---|
| 5,935,081 A | 8/1999 | Kadhiresan | 600/513 |
| 5,974,340 A * | 10/1999 | Kadhiresan | 607/18 |
| 6,126,611 A * | 10/2000 | Bourgeois et al. | 600/529 |
| 2002/0193697 A1* | 12/2002 | Cho et al. | 600/529 |
| 2003/0153953 A1* | 8/2003 | Park et al. | 607/17 |
| 2003/0153954 A1* | 8/2003 | Park et al. | 607/17 |
| 2003/0153955 A1* | 8/2003 | Park et al. | 607/17 |
| 2003/0153956 A1* | 8/2003 | Park et al. | 607/17 |
| 2003/0195571 A1* | 10/2003 | Burnes et al. | 607/9 |
| 2003/0204213 A1* | 10/2003 | Jensen et al. | 607/17 |
| 2004/0186523 A1* | 9/2004 | Florio | 607/17 |

FOREIGN PATENT DOCUMENTS

| | | |
|---|---|---|
| EP | 0 940 155 A2 | 9/1999 |
| EP | 0 940 155 B1 | 9/1999 |

\* cited by examiner

*Primary Examiner*—Mark W Bockelman
*Assistant Examiner*—Roland Dinga

(57) ABSTRACT

An implantable cardiac device minimizes apnea burden. In one implementation, the device administers a series of cardiac pacing trials using a different value for a pacing parameter in each trial and then measures an apnea burden corresponding to each trial in order to determine a value which reduces apnea burden when used for ongoing cardiac pacing. In one implementation the implantable cardiac device performs series of trials in cycles, during which a first series of trials determines a value for a first pacing parameter for reducing apnea burden while other pacing parameters are held constant. Subsequent series of trials subject the other pacing parameters, in turn, to their own series of pacing trials while holding the non-subjected pacing parameters constant. Through multiple cycles, the device optimizes each parameter in turn based on continually improving values for the other pacing parameters.

10 Claims, 7 Drawing Sheets

|  | Trial Rest Rate | Apnea Burden |
|---|---|---|
| Trial 1 602 | 70 ppm 604 | 40% 606 |
| Trial 2 608 | 75 ppm 610 | 25% 612 |
| Trial 3 614 | 78 ppm 616 | 29% 618 |
| Trial 4 620 | ? | ? |

*Fig. 6*

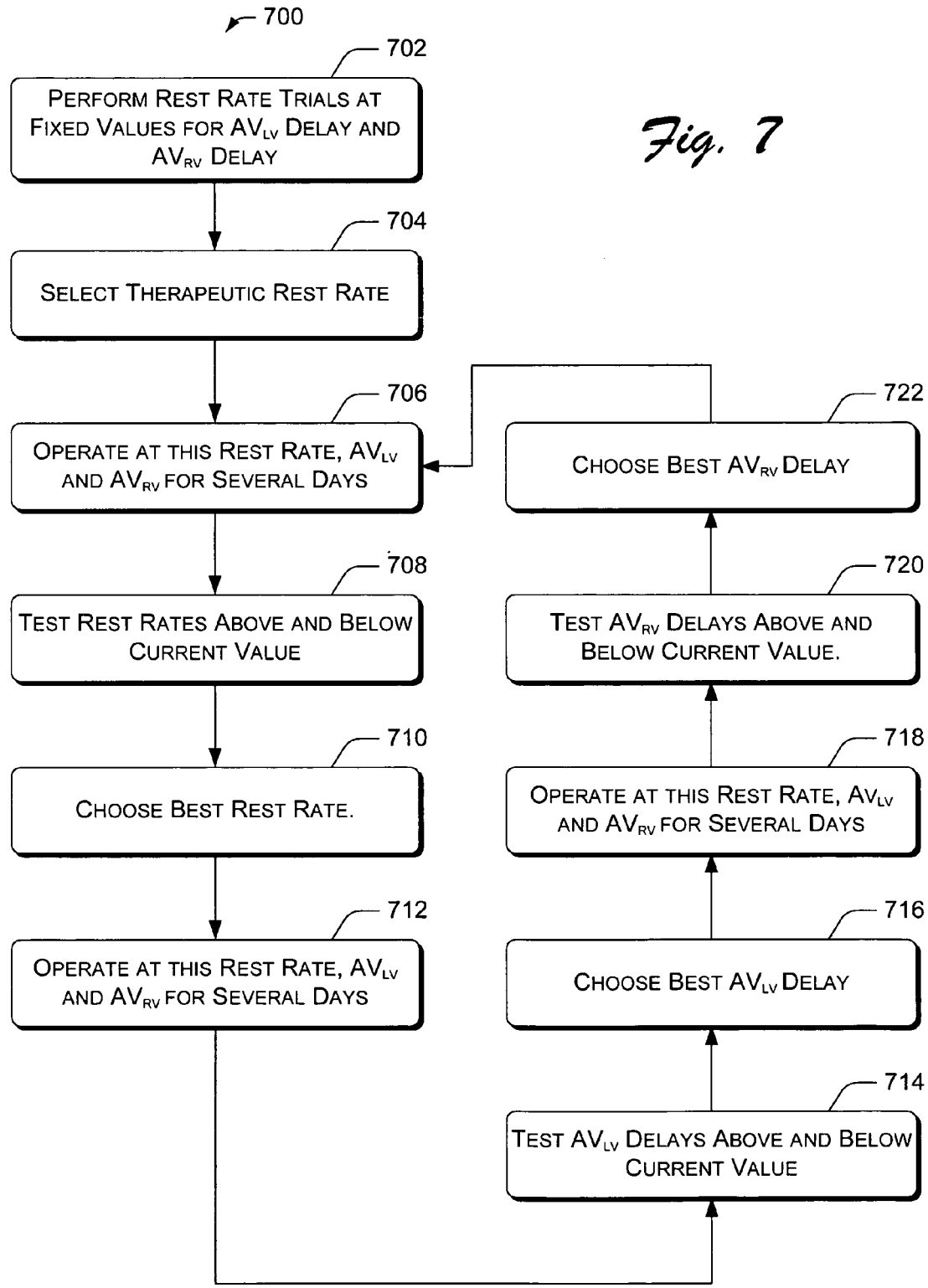

APNEA BURDEN MINIMIZING CARDIAC STIMULATION DEVICE

TECHNICAL FIELD

The present invention relates generally to implantable cardiac devices, and particularly, to a cardiac stimulation device that minimizes apnea burden.

BACKGROUND

Sleep apnea, a prevalent sleep disorder, manifests many undesirable symptoms that range from snoring, cessation of breathing, and headaches to depression, memory loss, and exacerbation of heart disease. "Hypopnea," a related malady that begets some of the same symptoms as apnea, refers to a breathing rate or tidal volume that is less than fifty percent of a patient's normal baseline breathing pattern.

Blood chemistry changes occur when apnea and hypopnea modify normal breathing during sleep. Breathing difficulty can cause blood oxygenation to fall to low levels and carbon dioxide and its derivatives to build up in the blood. When the control centers in the brain sense these chemical changes they often cause an arousal of the apneic patient. Thereafter, regular breathing and normal exchange of oxygen and accumulated carbon dioxide may resume—for a time, until the next episode.

Severe apnea and hypopnea result in hundreds of episodes of low oxygen levels per night. The typical apnea patient may have little awareness of the nightly struggle to breathe until its effects are felt the next day.

Sleep apnea can be classified as "obstructive" if caused by mechanical blockage of airflow, "central" if caused by central nervous system disorder, or "mixed" if a combination of obstructive and central.

Sleep apnea can be life-threatening if it occurs with coronary artery disease (CAD) or congestive heart failure (CHF—sometimes referred to as just "heart failure"). Not only does apnea directly place a load on the heart and cardiopulmonary system, but indirectly affects these organs by circumventing restful sleep. Alteration of sleep cycle phases causes sleep to be partly ineffective. A cycle of sleep debt and daytime weariness worsens CAD, CHF, and also hypertension. Consequently, sleep apneics who have a blood oxygen level lowered by sleep-disordered breathing are at increased risk for hypertension, arrhythmias, heart attack, stroke, and nocturnal sudden death.

Sleep apnea burden ("apnea burden") is a metric that may be defined in several ways. For example, the apnea burden may be proportional to the number of apneic and hypopneic episodes that occur per hour, sometimes called the Apnea Hypopneic Index (AHI). Other metrics of apnea burden are possible—for example, the total time spent in apnea and hypopnea per hour, the total time spent in apnea and hypopnea per night, or the frequency of arousal due to apnea and hypopnea per hour. In general, as used herein, "apnea burden" means the extent, severity, and/or gravity of the sleep apnea/hypopnea that a patient experiences, and is described in U.S. Pat. No. 6,741,885 to Park et al., entitled, "Implantable Cardiac Device for Managing the Progression of Heart Disease and Method," which is incorporated by reference herein.

Approximately fifty percent of patients with heart failure suffer concurrent sleep apnea. About ten percent of these heart failure patients suffer from obstructive sleep apnea, while about forty percent suffer from central sleep apnea. A high comorbidity exists between sleep apnea and CHF, which results from a negative synergy between problematic gas exchange during apnea and problematic oxygen distribution caused by weak cardiac pumping and fluid buildup characteristic of CHF.

CHF is a condition in which a weakened heart cannot provide enough pressure to prevent buildup of fluid in bodily tissues. CHF may affect either the right side, left side, or both sides of the heart. The weak pumping action causes fluid to back up into other areas of the body including the liver, gastrointestinal tract, and extremities (right-sided heart failure), or the lungs (left-sided heart failure). Heart failure patients have characteristic pulmonary edema or pitting edema of the lower legs.

Structural and functional causes of heart failure include high blood pressure (hypertension), valvular heart disease, congenital heart disease, cardiomyopathy, heart tumor, and other heart diseases. Precipitating and exacerbating factors include infections with high fever, anemia, irregular heartbeats (arrhythmias), hyperthyroidism, and kidney disease, and of course, sleep apnea. CHF and sleep apnea often occur together in a patient, as mentioned above, and exacerbate each other. Conversely, treating one usually improves the other.

Separately or in addition to the exemplary methods described herein, sleep apnea may be treated by administering continuous positive airway pressure (CPAP) or by various other treatments, such as surgery and medications. The type of treatment depends in part on the type of sleep apnea and personal preferences. It is generally believed that reducing heart failure symptoms reduces the apnea burden, which in turn further reduces the heart failure symptoms. Cardiac pacing therapy for diagnosing and treating sleep apnea is still relatively unexplored. Hence, there is a continuing need to improve the techniques for applying pacing therapy from implantable cardiac devices in a manner that effectively combats sleep apnea and heart failure.

SUMMARY

An implantable cardiac device administers a series of cardiac pacing trials using a different value for a pacing parameter in each trial and measures an apnea burden corresponding to each trial in order to determine a pacing parameter value which, when used for cardiac pacing, reduces apnea burden. In one implementation, the device conducts trials of pacing rates, measuring the sleep apnea burden associated with application of each pacing rate. From the trials, the device selects a pacing rate for ongoing sleep apnea therapy.

In another implementation, the implantable cardiac device performs multiple series of trials in cycles, during which a first series of trials determines a value for a first pacing parameter for reducing apnea burden while other pacing parameters are held constant. Subsequent series of trials subject each of the other pacing parameters, in turn, to their own series of pacing trials while holding the non-subjected pacing parameters constant. Through multiple cycles the device optimizes each parameter for reducing apnea burden in turn, based on continually improving values for the other pacing parameters.

BRIEF DESCRIPTION OF THE DRAWINGS

FIG. 6 is a table of example results from trials conducted to determine a value of a pacing parameter to reduce sleep apnea burden during cardiac pacing.

FIG. 7 is a flow diagram of an exemplary method for determining a value for each of multiple pacing parameters to reduce apnea burden during cardiac pacing.

DETAILED DESCRIPTION

Figure 1:
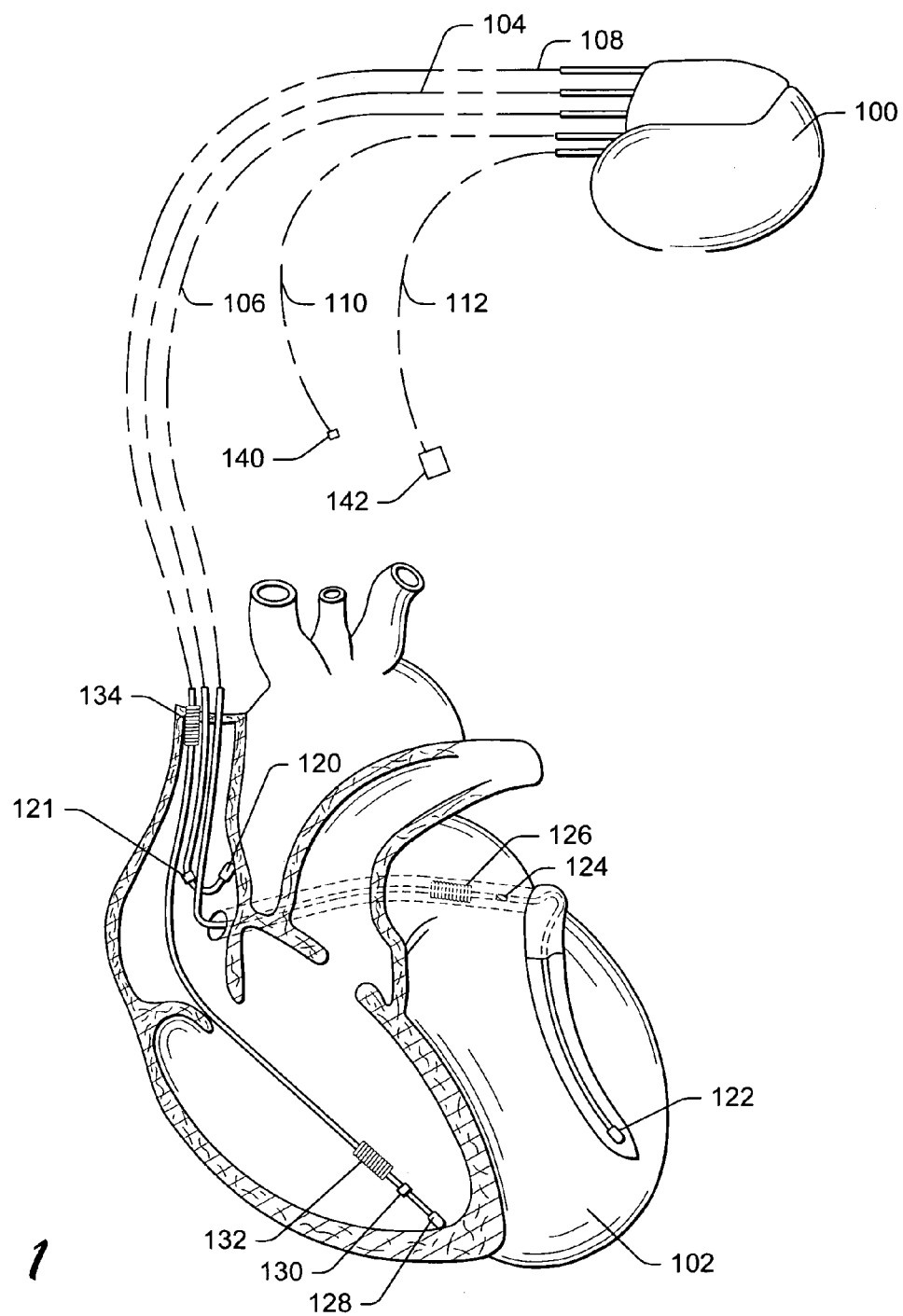
FIG. 1 is a diagram of an implantable cardiac device in electrical communication with a patient's heart for multi-chamber sensing and delivery of multi-chamber stimulation and shock therapy, as well as for conducting trials of pacing pulse characteristics for purposes of sleep apnea therapy.

In the following discussion, exemplary implantable cardiac devices and methods are described that treat sleep apnea, especially in patients experiencing at least some degree of heart failure (see, e.g., New York Heart Association "NYHA" classifications for CHF). In an exemplary method performable by a cardiac stimulation device, such as an implantable cardioverter defibrillator (ICD) or other implantable device, an exemplary ICD diagnoses the presence of sleep apnea and measures an apnea burden. A cardiac pacing parameter is then varied during multiple pacing trials while other cardiac pacing parameters are held constant. During and/or after each of the trials, the exemplary ICD again measures the apnea burden. By comparing the measured apnea burdens for each trial, the exemplary ICD finds the corresponding value for the pacing parameter (the one being varied) that results in the lowest apnea burden. Thus, an exemplary ICD can optimize or "tune" a pacing parameter to decrease a patient's apnea burden.

In one implementation the exemplary ICD performs series of trials in a cycle, during which a first series of trials determines a value for a first pacing parameter for reducing apnea burden while other pacing parameters are held constant. Subsequent series of trials subject each of selected other pacing parameters in turn to their own series of pacing trials while holding the non-subjected pacing parameters constant. Through multiple cycles the device continually tries to optimize values for the multiple pacing parameters for reducing apnea burden, wherein an improved value for one pacing parameter allows an improved value for the next pacing parameter in the cycle to be determined. In other words, the exemplary ICD uses a "hill-climbing technique" in which an improvement in a first of the selected parameters becomes a steppingstone for improving the second parameter in the sequence, and so on until an improvement in the last parameter in the sequence becomes a steppingstone for improving the first parameter, etc.

Because such an exemplary ICD and/or an exemplary method may calibrate many pacing parameters and periodically fine-tune them to an individual patient's needs, the device can aid in restoring and maintaining a patient's cardiac and respiratory homeostasis indefinitely.

In one implementation, an exemplary ICD posits initial therapeutic values for one or more pacing parameters to be applied during a time interval ("trial"), such as the pacing rate, atrioventricular (AV) delay, pulse width, waveform, pulse amplitude, etc. The duration of each trial may be an entire night or some other patient rest interval. The parameter values posited by the ICD may be pre-set or the ICD may use feedback provided by previous trials to select initial pacing parameter values for a current trial.

After a set number of trials, or when feedback indicates that no more reduction of apnea burden is likely, the exemplary ICD selects "best" "optimized" or "tuned" pacing parameter values from the trials for ongoing therapeutic use in reducing apnea burden. An exemplary ICD may optionally resume a trial administration mode at set intervals, such as biweekly, to fine tune pacing parameter values as the sleep apnea condition and the heart failure condition improve or otherwise change. Alternatively, the device can resume trials immediately when sensors detect subtle changes or slippage in monitored heart and apnea conditions. Further, if the device senses danger, a trial can be terminated.

The various exemplary devices and methods described herein use actual trial results specific to a patient for adjusting pacing parameters for that patient, rather than relying on general rule-of-thumb values for the pacing parameters, which may or may not be optimal for the individual patient with changing needs. The known and the as-yet undiscovered physiological variables that link heart failure morbidity with sleep apnea morbidity may or may not come into play for a given patient, thus it is better if the pacing parameters are customized for given patient at a given time. The best pacing may be that which minimizes apnea burden or it may be that which does not completely minimize apnea burden but provides other advantages, such as preventing the patient from frequently waking up during apnea therapy.

Cardiac Devices

An ICD can be characterized as a miniature computing device implanted into the body of a patient to monitor, regulate, and/or correct cardiac activity. Such devices include implantable cardiac stimulation devices (e.g., implantable cardiac pacemakers, rhythm converters, and implantable defibrillators) that apply stimulation therapy to the heart. The following discussion describes an exemplary ICD that is effective for treating heart conditions, such as those related to CHF, and for reducing apnea burden. The exemplary ICD can administer cardiac pacing trials, in which various values for a pacing parameter are tested, and select a therapeutic pacing parameter value to reduce apnea burden.

Exemplary ICD

FIG. 1 shows an exemplary ICD 100 in electrical communication with a patient's heart 102 for monitoring cardiac activity, delivering stimulation therapy, such as pacing therapies, and reducing apnea burden. Three leads—a right atrial lead 104, a coronary sinus lead 106, and a right ventricular lead 108—interconnect the exemplary ICD 100 with the patient's heart 102 to support multi-chamber detection and stimulation therapy. Additional leads may be used for other electrical and chemical sensors located inside or outside the heart.

The right atrial lead 104 supports an atrial tip electrode 120, which typically is implanted in the patient's right atrial appendage. The right atrial lead 104 also supports a right atrial ring electrode 121, which enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the exemplary ICD 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 may be used for shocking therapy.

The right ventricular lead 108 is electrically coupled to a right ventricular tip electrode 128, a right ventricular ring electrode 130, a right ventricular (RV) coil electrode 132, and a superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

A blood chemistry lead 110 is positioned to allow a blood chemistry sensor 140 to come in contact with the patient's blood. A suitable location may be in a major artery or a pulmonary vein, depending on the size and type of the blood chemistry sensor 140. Alternatively, the coronary sinus lead 106 could be used to couple a blood chemistry sensor 140 with the exemplary ICD 100. The type of blood chemistry sensor 140 and its specific location depends on the type of test being performed. A chemical sensor may test for pH level, oxygen saturation, carbon dioxide level, etc.

In some implementations, one or more apnea burden lead (s) 112 may be positioned to facilitate measurement of apnea burden via an apnea symptom sensor 142. Since there are multiple ways to measure apnea burden, placement of the lead(s) 112 depends on the sensor(s) selected. If transthoracic impedance is used to measure apnea burden, then apnea burden lead(s) 112 may not be needed if transthoracic impedance can be measured through other electrodes coupled with leads 104, 106, 108. If an apnea symptom being used as a measure of apnea burden involves, for example, abdominal or leg movements, then an apnea symptom sensor 142 may be motion detector placed outside the heart via lead(s) 112.

Figure 2:
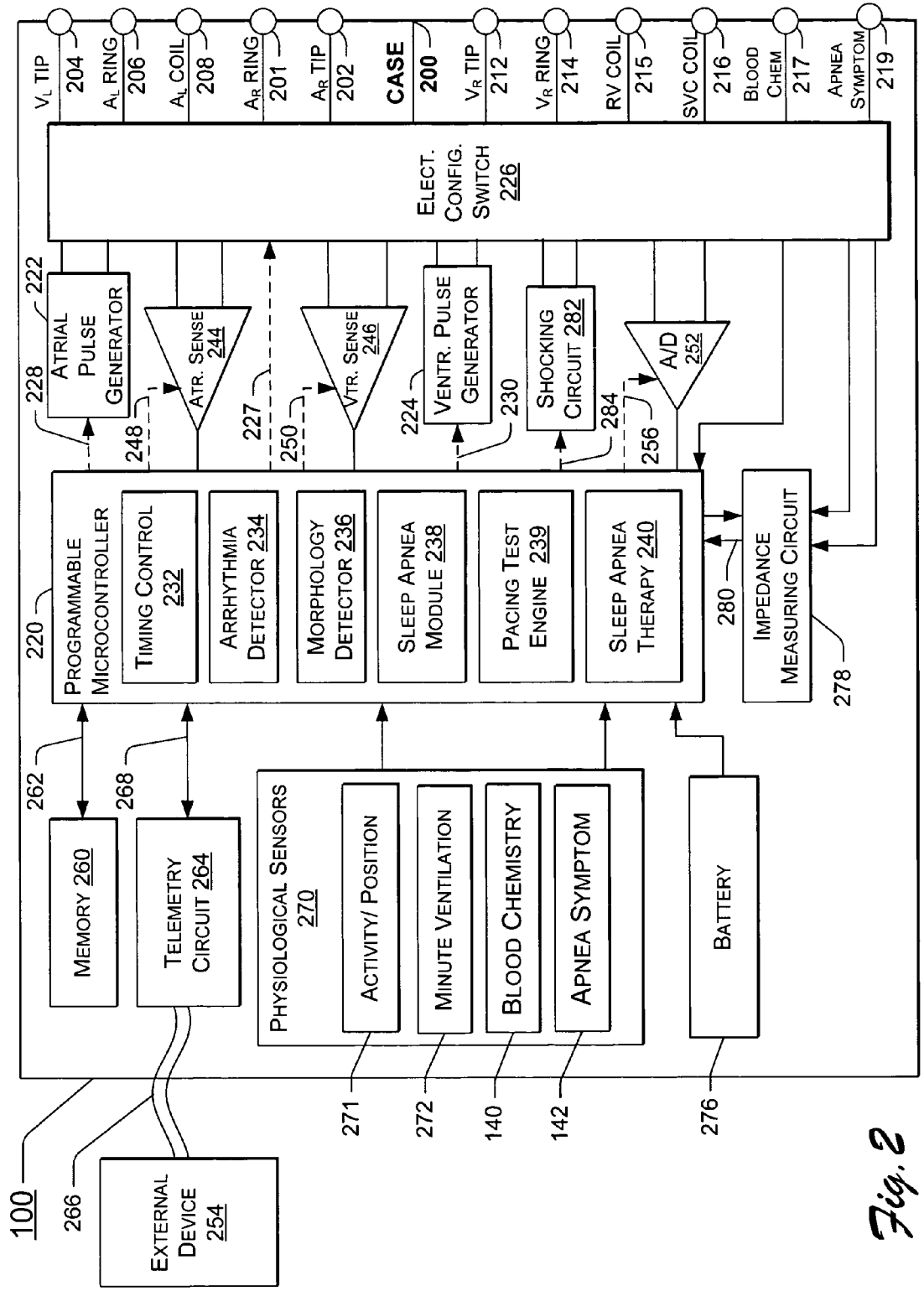
FIG. 2 is a functional block diagram of the multi-chamber implantable cardiac device.

FIG. 2 shows an exemplary block diagram depicting various components of the exemplary ICD 100. The components are contained in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 126, 132 and 134 for stimulating purposes. The case 200 further includes a connector (not shown) having a plurality of terminals (201, 202, 204, 206, 208, 212, 214, 215, 216, 217, and 219—shown schematically with the names of the electrodes to which they are connected shown next to the terminals), including:

a right atrial ring terminal (AR RING) 201 for atrial ring electrode 121;

a right atrial tip terminal (AR TIP) 202 for atrial tip electrode 120;

a left ventricular tip terminal (VL TIP) 204 for left ventricular tip electrode 122;

a left atrial ring terminal (AL RING) 206 for left atrial ring electrode 124;

a left atrial shocking terminal (AL COIL) 208 for left atrial coil electrode 126;

a right ventricular tip terminal (VR TIP) 212 for right ventricular tip electrode 128;

a right ventricular ring terminal (VR RING) 214 for right ventricular ring electrode 130;

a right ventricular shocking terminal (RV COIL) 215 for RV coil electrode 132;

an SVC shocking terminal (SVC COIL) 216 for SVC coil electrode 134 a blood chemistry terminal 217 for a blood chemistry sensor 140; and an apnea burden terminal 219 for an apnea symptom sensor 142.

An exemplary ICD 100 may include a programmable microcontroller 220 that controls various operations of the implantable cardiac device, including cardiac monitoring and stimulation therapy. Microcontroller 220 includes a microprocessor (or equivalent control circuitry), RAM and/or ROM memory, logic and timing circuitry, state machine circuitry, and I/O circuitry.

Exemplary ICD 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 220 is also equipped with an arrhythmia detector 234, a morphology detector 236, a sleep apnea module 238, and a sleep apnea therapy module 240.

The sleep apnea module 238 is configured to diagnose current episodes of sleep apnea and, in some implementations, even the onset of sleep apnea, thereby facilitating accurate measurement of sleep apnea, when it occurs. The sleep apnea module 238 also measures apnea burden. There are multiple ways of sensing sleep apnea and there are multiple metrics for apnea burden, for example, one metric might be time spent in apnea per hour. An exemplary sleep apnea module 238 uses measurements of one or more symptoms suggestive of apnea to measure apnea burden.

For instance, the detector might detect changes in respiration, heart rate, thoracic impedance, physical activity (abdominal movement, leg jerking), blood chemistry, and/or minute ventilation as being suggestive of sleep apnea. Frequent arousals from sleep are also indicative of sleep apnea and can be measured by an accelerometer, e.g., an activity/position sensor 271. In another approach, the sleep apnea module 238 detects coinciding changes of two or more parameters that indicate onset of sleep apnea and are viable for apnea burden measurements. For instance, a sleep apnea module 238 may anticipate an upcoming sleep apnea episode if the patient, while resting, experiences a decrease in minute ventilation and a concurrent drop in heart rate. In another approach, the sleep apnea module 238 uses pattern analysis to anticipate sleep apnea. The sleep apnea module 238 compares current physiological parameters with patterns of the same parameters captured during previous sleep apnea episodes to determine whether the current parameters suggest onset of sleep apnea.

If transthoracic impedance measurements are being used to diagnose sleep apnea or measure apnea burden, an exemplary sleep apnea module 238 may employ data from an impedance measuring circuit 278, and/or a minute ventilation sensor 272, to track breathing rate and/or tidal volume. If a change in blood chemistry is being used to diagnose sleep apnea or measure apnea burden, an exemplary sleep apnea module 238 may use in vivo measurements from a blood chemistry sensor 140 to detect an episode of sleep apnea and/or measure apnea burden. There are many chemical components of a patient's blood that change concentration, level, or saturation when the patient lapses into sleep apnea, such as oxygen, carbon dioxide, hydrogen ion, hydroxide ion, bicarbonate ion, etc. Each of these can be measured (e.g., pH, pOH, pCO2, O2 saturation, etc.) and compared to known thresholds or patient baseline values to diagnose the presence and/or duration of a sleep apnea episode. A blood chemistry sensor 140 may be selected to measure a concentration of a particular chemical or chemical species.

Alternatively, an exemplary sleep apnea module 238 may measure cardiac contractility in addition to or instead of other apnea symptoms as a surrogate for apnea burden. Cardiac contractility changes during episodic sleep apnea. Frequent changes in contractility are an indicator of apnea burden and an elevation in contractility often occurs late in an apnea cycle. Contractility and other surrogates of apnea burden can be measured using intracardiac impedance measurements (see U.S. Pat. No. 5,800,467 to Park and Bornzin), by an intracardiac accelerometer, or by an accelerometer in the pacemaker case 200 that measures the impulse associated with the first heart sound. Conventionally, contractility may also be measured by using an implantable pressure transducer that measures the maximum change in pressure as a function of time (dP/dt) in the right or left ventricle.

A sleep apnea therapy module 240 applies sleep apnea pacing therapy based on a programmed default and/or based on pacing parameter values determined by the exemplary pacing test engine 239 and/or exemplary techniques described herein for reducing apnea burden.

The components 232, 234, 236, 238, 239, and 240 may be implemented in hardware as part of the microcontroller 220, or as software/firmware instructions programmed into the device and executed on the microcontroller 220 during certain modes of operation. Although not shown, the microcontroller 220 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 104, coronary sinus lead 106, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power precision amplifiers with programmable gain and/or automatic gain control, bandpass filtering, and a threshold detection circuit to selectively sense the cardiac signal of interest. The automatic gain control enables the exemplary ICD 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 220 over signal lines 248 and 250 to control, for example, the gain and/or threshold of polarization charge removal circuitry (not shown) and the timing of blocking circuitry (not shown) optionally coupled to the inputs of the sensing circuits 244, 246.

Cardiac signals are supplied to an analog-to-digital (ND) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The data acquisition system 252 is coupled to the microcontroller 220, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

The microcontroller 220 is further coupled to a memory 260 by a suitable data/address bus 262. The programmable operating parameters used by the microcontroller 220 are stored in memory 260 and used to customize the operation of the exemplary ICD 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the ICD 100 may be non-invasively programmed into the memory 260 through a telemetry circuit 264 in telemetric communication via communication link 266 with the external device 254, such as a programmer, local transceiver, or a diagnostic system analyzer. The microcontroller 220 can activate the telemetry circuit 264 with a control signal 268. The telemetry circuit 264 allows intracardiac electrograms and status information relating to the operation of the exemplary ICD 100 (as contained in the microcontroller 220 or memory 260) to be sent to the external device 254 through an established communication link 266.

The exemplary ICD 100 can further include one or more physiological sensors 270, for example "rate-responsive" sensors that adjust pacing stimulation rates according to the exercise state of the patient. Accordingly, the microcontroller 220 responds by adjusting the various pacing parameters (such as rate, AV Delay, V-V Delay, etc.) at which the atrial and ventricular pulse generators 222 and 224 generate stimulation pulses.

Besides including sensors to detect sleep apnea and measure apnea burden as described above, the physiological sensors 270 may further include sensors detect changes in cardiac output, changes in the physiological condition of the heart, diurnal changes in activity (e.g., detecting sleep and wake states), G-force acceleration of the pacemaker case 200, length of the cardiac QT interval, changes in blood pressure, changes in temperature, respiration rate, and QRS wave duration. While shown as being included within the exemplary ICD 100, the physiological sensor(s) 270 may also be external to the exemplary ICD 100, yet still be implanted within or carried by the patient.

Illustrated physiological sensors 270 include an activity/position sensor 271 (e.g., 3D accelerometer, movement sensor, etc.) to detect changes in the patient's position and a minute ventilation (MV) sensor 272 to sense breathing. Minute ventilation can be measured as the total volume of air that moves in and out of a patient's lungs in a minute. The MV sensor 272 may use transthoracic impedance, which is a measure of impedance across the chest cavity, to sense air movement. Lungs filled with air have higher impedance than empty lungs. Thus, upon inhalation, impedance increases and upon exhalation, impedance decreases. A blood chemistry sensor 140 measures one or more selected chemicals, usually via a concentration, for example, pH, pOH, pC02, oxygen saturation, etc. Signals generated by the physiological sensors 270 are passed to the microcontroller 220 for analysis, e.g., by the sleep apnea module 238. Such signals can be used to determine whether the patient is at rest, whether the patient is experiencing an episode of sleep apnea, and to measure an apnea burden.

The exemplary ICD 100 additionally includes a battery 276 that provides operating power to all of the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also desirably has predictable discharge characteristics so that elective replacement time can be detected. As one example, the exemplary ICD 100 employs lithium/silver vanadium oxide batteries.

The exemplary ICD 100 can further include magnet detection circuitry (not shown), coupled to the microcontroller 220, to detect when a magnet is placed over the exemplary ICD 100. A magnet may be used by a clinician to perform various test functions of the exemplary ICD 100 and/or to signal the microcontroller 220 that an external programmer (e.g., 254) is in place to receive or transmit data to the microcontroller 220 through the telemetry circuits 264.

The exemplary ICD 100 further includes an impedance measuring circuit 278 that is enabled by the microcontroller 220 via a control signal 280. The impedance measuring circuit 278 is used for many things, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 278 may be coupled to the switch 226 so that any desired electrode may be used.

The exemplary ICD 100 may be operated as an implantable cardioverter/defibrillator device, which detects the occurrence of an arrhythmia and automatically applies an appropriate electrical shock therapy to the heart aimed at terminating the detected arrhythmia. To this end, the microcontroller 220 further controls a shocking circuit 282 via a control signal 284. The shocking circuit 282 generates shocking pulses of low (e.g., up to 0.5 joules), moderate (e.g., 0.5 to 10 joules), or high energy (e.g., 11 to 40 joules), as selected by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the case 200 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5 to 40 joules), delivered asynchronously (since R-waves may be too disorganized), and pertain exclusively to the treatment of fibrillation. Accordingly, the microcontroller 220 is capable of controlling the synchronous or asynchronous delivery of the shocking pulses.

The exemplary ICD 100 can be programmed to treat both heart failure and sleep apnea using pacing therapy. To treat heart failure, the device typically delivers pacing pulses of a voltage level via a lead in the left-sided veins.

More generally, the exemplary ICD 100 can be programmed to stimulate different sets of muscles through the same lead/electrode system. The exemplary ICD 100 can be programmed to vary the output voltage of various pulses to effectively stimulate different muscles of the heart, even though the lead and electrode placement does not change.

Pacing Therapy for Minimizing Apnea Burden

There are many pacing parameters that may affect apnea burden, such as pacing rate, atrioventricular (AV) delay, pulse width and waveform, pulse amplitude, etc. In the descriptions and figures below, if an exemplary method, device, or system is explained in terms of only one pacing parameter, such as pacing rate, other pacing parameters could be used as well. Thus, a pacing parameter used as an example is not meant to limit the description or figure to that pacing parameter. Likewise, while various exemplary methods described herein refer to an exemplary ICD 100, other analog and digital devices may also be suitable for implementation of the methods.

It should be noted that the eligibility of a pacing parameter to be tuned according to the described subject matter to reduce apnea burden may depend on the characteristics of a cardiac stimulation device already implanted in a patient.

Figure 3:
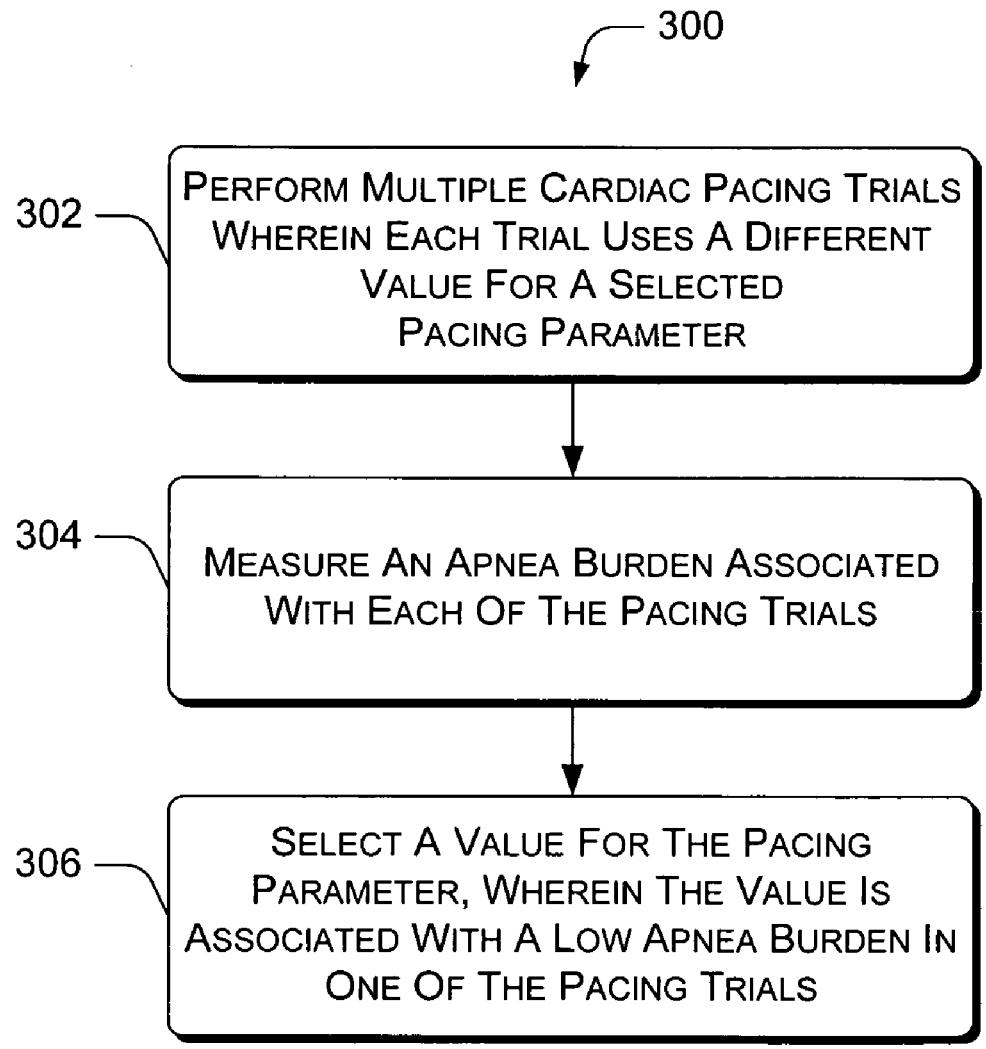
FIG. 3 is a flow diagram of a first exemplary method for determining a value of a pacing parameter to reduce apnea burden during cardiac pacing.

FIG. 3 shows a first exemplary method 300 for determining a value for a pacing parameter to reduce apnea burden during cardiac pacing. In the flow diagram for the exemplary method 300, the operations are summarized in individual blocks. The exemplary method 300 may be performed in analog or digital hardware and/or as machine-readable instructions (software or firmware) that can be executed by a processor, such as a microcontroller 220. Thus, the operations of the exemplary method 300 may be performed by one or more components of an ICD, such as a pacing test engine 239 in exemplary ICD 100.

In block 302, multiple cardiac pacing trials are performed. Each trial uses a different value for a selected pacing parameter. For example, the selected pacing parameter can be the pacing rate. If so, each pacing rate within the multiple cardiac pacing trials is applied for a time interval. In an exemplary application, a sequence of pacing rates to use in the trials can be predetermined according to a protocol. For example, the sequence might include every pacing rate in an allowed range, e.g., from 60 pulses per minute (ppm) to 90 ppm in increments of five: e.g., 60, 65, 70, 75, 80, 85, and 90 ppm or, in another example, every pacing rate in an allowed range from 70 ppm to 80 ppm in increments of one: e.g., 70, 71, 72 ppm, etc. As the sequence progresses, one of the pacing rates is administered during each time interval.

In block 304, an apnea burden associated with each trial is measured. Depending on what metric is used for apnea burden, as discussed above, the apnea burden measurement may involve sensing the frequency and/or the duration of breathing cessation, breathing decrease, frequency of arousal, etc.

In block 306, a value for the parameter being tested, i.e., a value associated with a low apnea burden, is adopted for ongoing cardiac pacing therapy. For example, if the pacing parameter being tested is pacing rate, then the pacing rate adopted for ongoing therapy may be that pacing rate that resulted in the lowest apnea burden during a trial. Alternatively, the pacing rate for ongoing therapy may be selected or extrapolated using the trial results and additional criteria, such as analysis of former sets of trial results for the particular patient, consideration of textbook pacing rate values, other patient history, compatibility with overall pacing regimens, concurrent physiological measurements and medications, etc.

Figure 4:
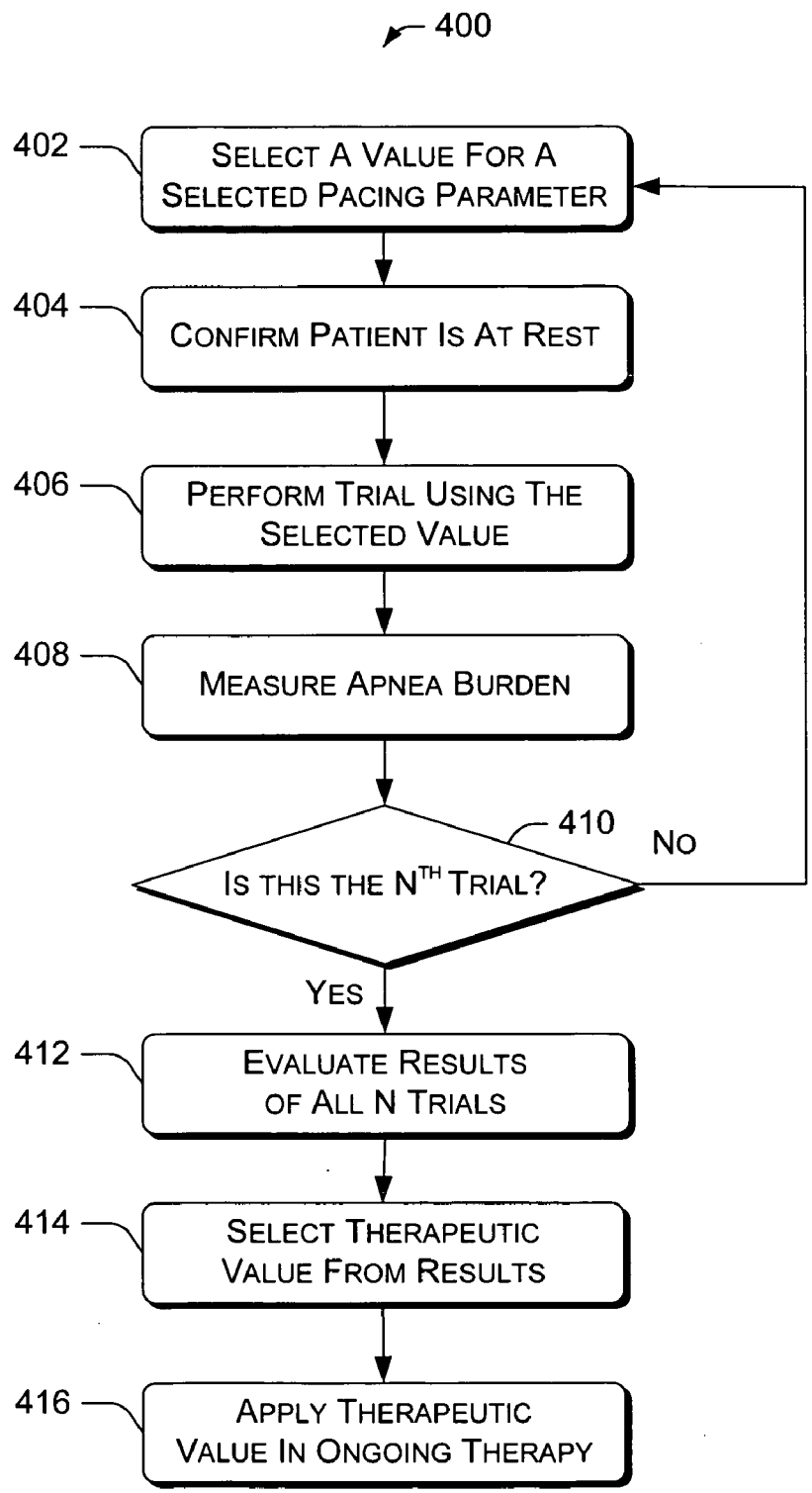
FIG. 4 is a flow diagram of a second exemplary method for determining a value of a pacing parameter to reduce apnea burden during cardiac pacing.

FIG. 4 shows another exemplary method 400 for finding and/or adjusting a value of a pacing parameter to reduce apnea burden during cardiac pacing. According to this exemplary method 400, an exemplary ICD 100 is programmed to perform cardiac pacing trials in which a pacing parameter is varied to find the "best," "optimized," or "tuned" value for the pacing parameter to reduce apnea burden for a given patient.

In the flow diagram for the exemplary method 400, the operations are summarized in individual blocks. The exemplary method 400 may be performed in analog or digital hardware and/or as machine-readable instructions (software or firmware) that can be executed by a processor, such as a microcontroller 220. Thus, the operations of the exemplary method 400 may be performed by one or more components of a cardiac stimulation device, such as pacing test engine 239 in an exemplary ICD 100.

At block 402, the exemplary ICD 100 selects a value for a selected pacing parameter from a range of allowable values. For example, if the selected pacing parameter is a pacing rate then an initial value may be selected from within a range of 60 ppm to 90 ppm, which is a reasonable range of base rates for "at rest" pacing. An allowable range for pacing parameter adjustment may be prescribed by a practitioner and programmed into the exemplary ICD 100. If a telemetry link 266 is active, the exemplary ICD 100 may consult an information resource, such as a record of patient characteristics or contemporaneous physiological measurements, when selecting a first trial rest rate from the allowed range.

In a variation, an exemplary ICD 100 does not consult an information resource for an initial value of a pacing parameter, but instead is programmed to perform a predetermined sequence of trials that uses a predetermined sequence of values for the pacing parameter that is to be optimized to reduce apnea burden. For example, an exemplary ICD 100 may be pre-programmed to perform six trials at pacing rates of 60, 65, 70, 75, 80, and 85 ppm, and then executes all six trials regardless of apnea burden results from individual trials. At the end of the six trials, the exemplary ICD 100 then evaluates the results to select the best value for the pacing parameter under test.

At block 404, the exemplary ICD 100 confirms that a patient is "at rest" using a standard definition of rest that is useful in the art of cardiac pacing, for example, rest as defined in U.S. Pat. No. 5,576,483 to Bornzin. There are many ways to implement the determination of the patient being at rest. One approach is to monitor signals from a position/posture sensor 272 to identify when the patient stops moving for a prolonged period of time, or when the patient reclines to a supine position. Another approach is to monitor a raw activity signal from the accelerometer and derive an activity variance parameter from the activity signal. One or both of the activity signal and the activity variance signal is then used to detect different patient states, such as resting and non-resting states.

At block 406, a trial is performed using the selected value for the pacing parameter under adjustment, that is, pacing is performed on the patient for a trial time interval. In one implementation, pacing pulses are applied for an entire night's sleep or patient rest period. In another implementation, the trial interval may be adjustable so that multiple trials can be performed during a single night or so that one trial lasts for several days.

A trial interval can be shortened if the exemplary ICD 100 senses radical changes in a patient's condition or an alarming increase in sleep apnea. Worsening of a heart condition and/or of the apnea can cause an exemplary ICD 100 to abort a trial and return to a normal pacing mode or a remedial pacing mode if danger is likely sensed.

At block 408, the exemplary ICD 100 measures the apnea burden associated with the trial rest rate, as discussed above.

At block 410, the exemplary ICD 100 may be preset to count the trials as they occur. Thus, if the set of trials is not complete, the method loops back to block 404, to select a new trial rest rate. When the Nth trial is reached the method branches to block 412, where the results of all N trials are evaluated.

In the illustrated exemplary method 400, the evaluation 412 may include examining the apnea burden associated with each trial and noting the value of the pacing parameter that was being tuned in each trial. The evaluation 412 may also include discarding trials with aberrant values, such as apnea burden measurements that are too high (e.g., a value for the selected pacing parameter was obviously counter-effective) or too low (e.g., there was little apnea burden because a value for the selected pacing parameter resulted in pacing that kept the patient awake). The evaluation 412 may include a filter routine for choosing between disparate values for the selected pacing parameter that both yielded the same low apnea burden measurement. For example, if the selected pacing parameter to be optimized is pacing rate, then from the set of trial rest rates 60, 65, 70, 75, 80, and 85 ppm, perhaps 60 and 80 each yield an apnea burden minimum. The exemplary ICD 100 can be programmed to select only one of these values as a best value or conduct further trials to discriminate between the two values.

The apnea burden measurements may be plotted against the associated pacing parameter values and/or subjected to statistical analysis if enough readings are taken, to find patterns in the data or to extrapolate a therapeutic pacing parameter value. In other words, the best or "tuned" value for a pacing parameter does not always have to be one of the values used directly in a trial, but can be derived from analysis of multiple trials. If an analyzable pattern is detected in the trial results, the results may be fitted or filtered against "textbook" examples of known patients with similar patterns to find an improved pacing parameter value. Data from the trials may be used in numerous ways to the patient's advantage, as discussed below in the description of other exemplary methods.

At block 414, the exemplary ICD 100 selects a therapeutic value for the selected pacing parameter, that is, the value that reduced apnea burden the most during the trials or otherwise seems best suited to the patient's needs. As mentioned above, the selection may simply entail finding the pacing parameter value that has the lowest associated apnea burden measurement, or it may entail finding the pacing parameter value that harmonizes with more complex considerations, such as lowest apnea burden combined with lowest rate of arousal, etc.

At block 416, the therapeutic value for the pacing parameter selected at block 414 is applied to the patient for a therapy interval. The therapy interval may be preprogrammed; for example, two weeks of therapy using the selected therapeutic rest rate followed by another set of trials. Alternatively, the therapy interval may be variable and depend on an exemplary ICD 100 to monitor cardiac and other physiological variables to initiate a set of trials whenever beneficial or necessary. The exemplary ICD 100 may also tune pacing parameters having to do with the best manner of applying another tuned pacing parameter value. For example, one pacing parameter can be which electrode placement gives optimal results for applying a tuned pacing rate.

Figure 5:
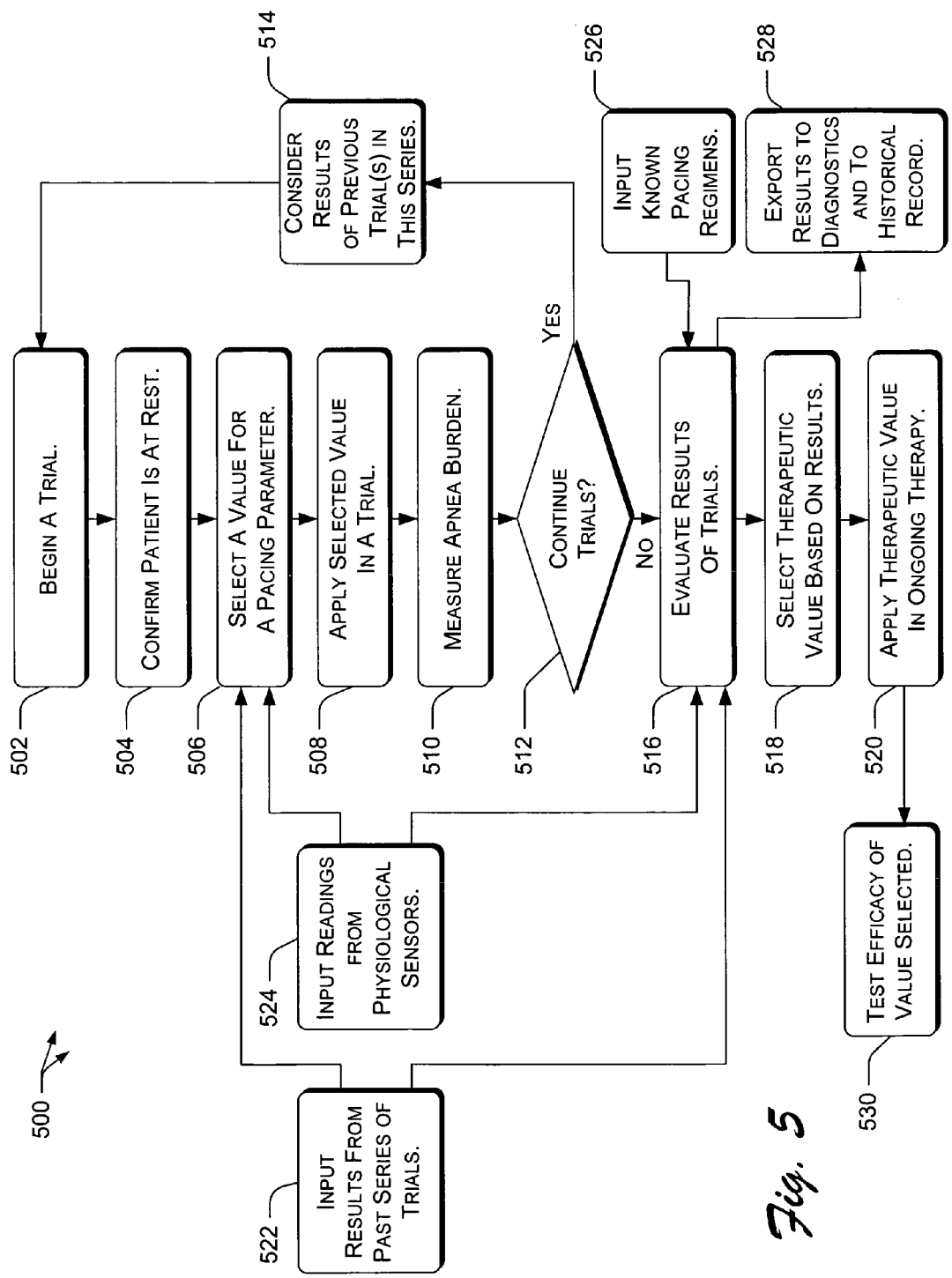
FIG. 5 is a flow diagram of a third exemplary method for determining a value of a pacing parameter to reduce apnea burden during cardiac pacing.

FIG. 5 shows a third exemplary method 500 for finding and/or adjusting a value of a pacing parameter to reduce apnea burden during cardiac pacing. According to this exemplary method 500, trials are performed as described above with respect to FIG. 4, however the exemplary method 500 is self-regulating and may continue indefinitely in some implementations by using one or more information feedback loops.

At block 502, a new trial is started to apply a selected value for a pacing parameter to a patient's heart and to measure an associated apnea burden during and/or after the trial. This new trial (at block 502) may be initiated for various reasons, for example, because some change has been sensed in the patient, or as part of a scheduled regimen.

At block 504, confirmation is made that the patient is at rest. This may be performed as described above for block 402 of FIG. 4. A determination that sleep is likely imminent or is likely occurring is usually a condition for measuring apnea burden.

At block 506, a trial value for the pacing parameter is selected. In one implementation, an initial value may be selected based on results from past series of trials at block 522 and/or feedback from physiological sensors 270 at block 524. These information sources allow an initial value to be selected based on history and/or the patient's current status, rather than a random value selection from an allowed range. However, the latter can be used for a new patient, e.g., to triage the new patient's response to various pacing parameter values.

At block 508, the selected value is applied in a trial.

At block 510, the apnea burden is measured, e.g., during and/or after the current trial.

At block 512, the exemplary ICD 100 decides if the trials should continue. The decision may be based on different criteria. In one scenario, the exemplary ICD 100 may spot a trend (e.g., raising a pacing parameter lowers apnea burden) and conclude that according to the trend a best value for a pacing parameter has already been determined. For example, further pacing parameter values in the direction of the trend do not yield a further reduction in apnea burden. If the trials are to continue, the exemplary method 500 branches to block 514, but if the trials are not to continue, then the exemplary method 500 branches to block 516, where results are evaluated.

At block 514, if the trial being initiated follows another trial in a current series of trials, then results of previous trial(s) in the series can be considered in selecting the value for the pacing parameter being tuned. For example, to zero in on a best value for a pacing parameter, an implementation of the exemplary method 500 may halve increments between values to be used in the trials, i.e., the exemplary method 500 may proceed from a rough-tuning phase (e.g., the next pacing rate value for a trial is 10 ppm higher than the last pacing rate used in a trial) to a fine-tuning phase (e.g., the next pacing rate value for a trial is 5 ppm higher or lower than the last pacing rate used in a trial).

The informed selection, based on previous results, of each new trial value for a pacing parameter such as pacing rate allows an exemplary ICD 100 to manage a patient's apnea burden and heart failure in an ongoing regimen by first, responding to current heart failure and sleep apnea symptoms, and second, by responding to new imbalances as they arise. In other words, the exemplary ICD 100 finds a therapeutic value for a pacing parameter from actual trial results and self-adjusts as the symptoms change without necessarily having to try to figure out theoretical relationships between multiple complex factors that may be causing the sleep apnea and the heart failure.

At block 516, the results of a series of trials are evaluated. Past results (as at block 522) and sensor input (as at block 524) may assist in the evaluation of a series of parameter trials and the results of the series of trials just completed may be given more weight than earlier trials. In considering past series of trials, as shown in block 522, a long-term trend may become evident when current results are compared with multiple past series of trials.

As mentioned, the evaluation at block 516 may also receive input from physiological sensors 270, as shown in block 524, that is, from sensors measuring conditions and physiological variables other than apnea burden. For example, in the case of a pacing rate parameter, a current ventilation sensor and a current heart rate sensor can be configured to measure the respiratory modulation of heart rate known as respiratory sinus arrhythmia (RSA) as a factor to consider in the evaluation at block 516. RSA is a change in heart rate during breathing due to inhalation and exhalation. The heart rate increases during inhalation and decreases during exhalation, an effect that appears to be greater in younger and in athletic individuals. Its presence in a patient could indicate to an exemplary ICD 100 that therapeutic changes in the pacing rate are more or less likely to affect apnea burden.

Similarly, known pacing regimens, as at block 526, may be consulted in the evaluation. For example, in one implementation, an exemplary ICD 100 may only perform two trials using two values for a selected parameter and extrapolate or distinguish a best value for the pacing parameter from known pacing regimens.

At block 518, a therapeutic "best," "optimized," or "tuned" value is selected as a therapeutic value for ongoing use. The selection of a best value may involve few steps, such as choosing the pacing parameter value with the lowest associated apnea burden, or it may involve more analytical steps, such as statistical analysis, curve tracing, differential analysis of maxima-minima and/or related rates, comparisons with known pacing regimes, comparison of past historical results, comparison of long and short term trends, etc. The technique used to make the selection at block 518 may depend on the quantity and quality of data collected and/or produced in the evaluation at block 516.

At block 520, the selected value is applied in ongoing therapy, either for a predetermined interval of time according to a schedule, or for an indefinite interval during which the exemplary ICD 100 monitors for changes that would warrant a resumption of trials, such as maintenance trials.

At block 528, the results of the evaluation of results at block 516 can be exported to diagnostic or historical entities, such as the patient's electronic chart.

At block 530, the efficacy of the value selected with respect to reducing apnea burden can be further tested. In some cases, the selected value can be double-checked or rechecked at regular intervals, as the patient's health changes. In one implementation, efficacy of a selected therapeutic value may be tested by administering a mini-series of one or two trials and adjusting if necessary. An exemplary method can periodically adjust a pacing parameter, apply a number of pacing pulses for each adjustment to the pacing parameter, measure an apnea burden associated with each adjustment, and select one of the pacing parameter values based on an associated apnea burden. For example, in one implementation, a first trial uses a value for the pacing parameter in question that is slightly higher than the current therapeutic value selected from previous trials and the second trial of the mini-series uses a value that is slightly lower than the current therapeutic value. If either the higher or the lower trial rest rates result in a lower apnea burden than that associated with the current therapeutic rest rate, the exemplary ICD 100 adopts the more efficacious value for reducing apnea burden. The exemplary ICD 100 can continue to adjust itself to a patient's needs in this manner indefinitely.

FIG. 6 is an exemplary table 600 showing results from three pacing trials. An exemplary ICD 100 can use these or similar results to select a pacing parameter value for a next trial (corresponding to block 514 in FIG. 5), in this case a fourth trial 620. The illustrated exemplary table 600, which uses pacing rate as an example of a pacing parameter to be optimized in order to reduce apnea burden, is for illustrative purposes; a table of actual patient results may vary from table 600.

In the first trial 602, a first pacing rate 604 of 70 ppm is applied and an associated apnea burden 606 is measured at 40% (where, for example, apnea burden is defined as the percentage of time a patient is in apnea/hypopnea during the trial). During a second trial 608, a second pacing rate 610 of 75 ppm is applied and the associated apnea burden measurement 612 is 25%, i.e., a 15% reduction (improvement) from the previous trial. During the third trial 614, a trial pacing rate 616 of 78 ppm is applied and the associated apnea burden measurement 618 is 29%, a 4% increase in apnea burden (a worsening) from the second trial 608 even though the third trial pacing rate 616 of 78 ppm, was higher than the previous trial rest rate 610 and was expected to continue the trend of further improvement (but did not). For a fourth trial 620, the exemplary ICD 100 can select a new trial pacing rate closer to the current minimum apnea burden established on the second trial 608, for example the exemplary ICD 100 can select 76 ppm, 74 ppm, or can even retry 75 ppm again to verify results.

The exemplary table 600 of FIG. 6 shows that through multiple trials, an exemplary ICD 100 can begin building a database that relates a selection of values for a pacing parameter to a measured apnea burden corresponding to each value in the selection. Once the database is established, apnea burden maxima and minima can be discovered through various methods which can range from a simple numerical sort of resulting apnea burden measurements to more complex and elaborate curve analysis, etc.

FIG. 7 shows an exemplary method 700 for determining multiple pacing parameter values to reduce apnea burden. A series of cardiac pacing trials are performed in a cycle, during which a first series of trials determines a value for a first pacing parameter for reducing apnea burden while other selected pacing parameters are held constant. Subsequent series of trials subject each of the other pacing parameters in turn to their own series of pacing trials while holding the non-subjected pacing parameters constant. Through multiple cycles the device continually tries to optimize values for the multiple pacing parameters in order to reduce apnea burden. An improved value for one pacing parameter allows an improved value for the next pacing parameter in the cycle to be determined, and so on through the cycles.

In the flow diagram for the exemplary method 700, the operations are summarized in individual blocks. The exemplary method 700 may be performed in analog or digital hardware and/or as machine-readable instructions (software or firmware) that can be executed by a processor, such as a microcontroller 220. Thus, the operations of the exemplary method 700 may be performed by a pacing test engine 239 in an exemplary ICD 100.

By staggering the adjustment of each pacing parameter being managed, the patient is spared sudden cardiac and respiratory imbalance. Interactions between the multiple pacing parameters are groomed over time by the exemplary ICD 100 so that each pacing parameter becomes individually fine-tuned and in some instances allows better fine-tuning of other pacing parameters, particularly if the pacing parameters are dependent on each other.

At block 702 an exemplary ICD 100 performs a series of trials on a first pacing parameter, such as pacing rate, that affects apnea burden. Other pacing characteristics to be managed, for example, left ventricular AV delay (AVLV) and right ventricular AV delay (AVRV), are fixed for the current trials at acceptable values. The series of trials (702) on the first pacing parameter may be performed as illustrated in FIGS. 3-5. At block 704, an exemplary ICD 100 selects a current therapeutic pacing rate.

At block 706, the exemplary ICD 100 operates at the current therapeutic rest rate and the fixed AVLV delay and AVRV delay for a selected therapeutic time interval, such as several days or weeks.

At block 708, the exemplary ICD 100 optionally tests the efficacy of the current therapeutic pacing rate (that is, the first pacing parameter). For example, the exemplary ICD 100 may test the efficacy of the current pacing rate by testing pacing rates immediately above and immediately below the current therapeutic pacing rate, selected at block 704.

At block 710, if one of the pacing rates at block 708 lowers the apnea burden more efficaciously than the current therapeutic pacing rate, the better rate is selected.

At block 712, the exemplary ICD 100 now applies whichever pacing rate is selected as the most efficacious for reducing apnea burden also using the fixed AVLV delay and AVRV delay for another selected therapeutic time interval.

At block 714, the exemplary ICD 100 tests the efficacy of a second pacing parameter, in this case, the AVLV delay. The exemplary ICD 100 may test the efficacy of a current AVLV delay value by testing AVLV delay values immediately above and immediately below the currently selected therapeutic value.

At block 716, the most efficacious AVLV delay value from block 714 is selected.

At block 718, the exemplary ICD 100 now applies therapeutic pacing for another selected therapeutic time interval at whichever AVLV delay value is selected as most efficacious for reducing apnea burden and also using the currently selected pacing rate and the currently fixed value of AVRV delay.

At block 720, the exemplary ICD 100 tests the efficacy of a next pacing parameter, in this case, a third pacing parameter: the AVRV delay. The exemplary ICD 100 may test the efficacy of a current AVRV delay value by testing AVRV delay values immediately above and immediately below the currently selected therapeutic value.

At block 722, the most efficacious AVRV delay value for reducing apnea burden is selected.

The cycle may now return to block 706, where the exemplary ICD 100 now operates for another selected therapeutic time interval at whichever AVRV delay value is selected at block 722 as most efficacious for reducing apnea burden and also using the currently selected pacing rate and the currently selected AVLV delay value.

The exemplary method 700 illustrated in FIG. 7 may continue indefinitely in order to manage multiple pacing parameters that affect a patient's apnea burden and perform fine-tuning of the multiple pacing parameters.

It should be noted that the exemplary method 700 is only one example implementation of how the subject matter can be used to manage multiple pacing parameters that affect apnea burden. There are many other ways an exemplary method according to the subject matter can be arranged. For example, the number of pacing parameters being managed can vary, and the manner of fine-tuning the each pacing parameter may be different. For example, at blocks 708, 714, and 720 an exemplary ICD 100 could perform a complete series of fresh trials (as at block 702) for each pacing parameter that comes due for a tune-up in the cycle shown in FIG. 7, instead of just testing parameter values immediately above and below the expiring therapeutic value.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An implantable cardiac device, comprising:
  pacing circuitry to apply pulses to a patient's heart using multiple physiologic pacing parameters;
  a pacing test engine to periodically select trial values for one of the multiple physiologic pacing parameters and for each trial value to apply the pulses using the trial value for a time interval;
  an apnea detector to measure an apnea burden associated with each time interval; and
  an apnea therapy module to receive apnea burden measurements and select a value for a pacing parameter based on the trial values and associated apnea burdens, wherein the apnea therapy module is configured to determine the corresponding value for the pacing parameter that results in a lowest apnea burden and to direct the pacing circuitry to apply the corresponding value during pacing;
  wherein the sleep apnea detector measures apnea burden by measuring cardiac contractility.

2. The implantable cardiac device as recited in claim 1, wherein one of the multiple physiologic pacing parameters comprises a pacing rate.

3. The implantable cardiac device as recited in claim 1, wherein one of the multiple physiologic pacing parameters comprises an atrioventricular delay.

4. The implantable cardiac device as recited in claim 1, wherein:
  the sleep apnea detector measures an apnea burden associated with each of multiple trial values; and
  the pacing test engine selects a new trial value based on a comparison of the apnea burdens.

5. The implantable cardiac device as recited in claim 4, wherein the pacing test engine compares the apnea burdens with known pacing regimens to select the new trial value.

6. The implantable cardiac device as recited in claim 4, wherein the pacing test engine compares the apnea burdens with past pacing test results of the patient to select the new trial value.

7. The implantable cardiac device as recited in claim 1, wherein the cardiac contractility is measured by one of an impedance sensor, an accelerometer, and a pressure transducer.

8. The implantable cardiac device as recited in claim 1, wherein one of the multiple physiologic pacing parameters comprises a pulse width.

9. The implantable cardiac device as recited in claim 1, wherein one of the multiple physiologic pacing parameters comprises a pulse amplitude.

10. The implantable cardiac device as recited in claim 1, wherein one of the multiple physiologic pacing parameters comprises a waveform.

* * * * *